(12) United States Patent
Tajima

(10) Patent No.: US 6,906,338 B2
(45) Date of Patent: Jun. 14, 2005

(54) LASER DRIVEN ION ACCELERATOR

(75) Inventor: Toshiki Tajima, Alamo, CA (US)

(73) Assignee: The Regents of the University of California, Oakland, CA (US)

( * ) Notice: Subject to any disclaimer, the term of this patent is extended or adjusted under 35 U.S.C. 154(b) by 427 days.

(21) Appl. No.: 09/757,150

(22) Filed: Jan. 8, 2001

(65) Prior Publication Data

US 2002/0090194 A1 Jul. 11, 2002

Related U.S. Application Data

(60) Provisional application No. 60/224,386, filed on Aug. 9, 2000.

(51) Int. Cl.[7] ................................................. H01J 27/24
(52) U.S. Cl. ............................... 250/505.1; 250/396 R; 250/398; 250/423 R; 315/500; 315/505; 315/111.61
(58) Field of Search .......................... 250/505.1, 396 R, 250/398, 423 R; 315/500, 505, 111.61

(56) References Cited

U.S. PATENT DOCUMENTS

| | | | |
|---|---|---|---|
| 4,069,457 A | 1/1978 | Martin et al. ................ 328/235 |
| 4,215,274 A | * 7/1980 | Segall ..................... 250/361 R |
| 4,471,224 A | 9/1984 | Cuomo et al. ............... 250/423 |
| 4,715,038 A | 12/1987 | Fraser et al. .................... 372/2 |
| 4,937,532 A | 6/1990 | Dawson et al. ............... 330/4.3 |
| RE34,575 E | 4/1994 | Klinkowstein et al. ...... 315/500 |
| 5,335,258 A | 8/1994 | Whitlock ..................... 378/122 |
| 5,339,347 A | * 8/1994 | Slatkin et al. ................. 378/65 |
| 5,382,914 A | 1/1995 | Hamm et al. ................ 315/505 |
| 5,394,411 A | 2/1995 | Milchberg et al. .............. 372/5 |
| 5,412,283 A | 5/1995 | Trone ......................... 315/5.41 |
| 5,440,133 A | 8/1995 | Moyers et al. ............ 250/492.3 |
| 5,576,593 A | * 11/1996 | Schultheiss et al. .... 313/231.31 |
| 5,789,876 A | * 8/1998 | Umstadter et al. ........... 315/507 |
| 5,930,331 A | * 7/1999 | Rentzepis et al. ........... 378/136 |
| 2003/0183774 A1 | * 10/2003 | Tajima .................... 250/423 P |

FOREIGN PATENT DOCUMENTS

| | | |
|---|---|---|
| DE | 3616879 | 11/1986 |
| JP | 6068984 A | 3/1994 |
| JP | 7169597 A | 7/1995 |

OTHER PUBLICATIONS

T.E. Cowan, et al., "Photo–Nuclear Fission from High Energy Electrons from Ultra–Intense Laser–solid Interactions," UCRL–JC–137795, Jul. 13, 1999, 15 pages.

T.E. Cowan, "High Energy Electrons, Nuclear Phenomena and Heating in Petawatt Laser–Solid Experiments," UCRL–JC–133031 Preprint, Jan. 15, 1999, 13 pages.

B. Rau, et al.,"Strongly Nonlinear Magnetosonic Waves and Ion Acceleration," American Institute of Physics, vol. 5, No. 10, Oct. 1998, page(s) 3575–3580.

H. Hojo, et al., "Particle Acceleration and Coherent Radiation by Subcycle Laser Pulses," Nuclear Instruments & Methods in Physics Research, A 410, (1998) page(s) 509–513.

* cited by examiner

*Primary Examiner*—Nikita Wells
(74) *Attorney, Agent, or Firm*—Eddie E. Scott; Christopher J. Horgan; Alan H. Thompson

(57) ABSTRACT

A system and method of accelerating ions in an accelerator to optimize the energy produced by a light source. Several parameters may be controlled in constructing a target used in the accelerator system to adjust performance of the accelerator system. These parameters include the material, thickness, geometry and surface of the target.

11 Claims, 8 Drawing Sheets

LASER DRIVEN ION ACCELERATOR

RELATED APPLICATION

This application relates to U.S. Provisional Application No. 60/224,386 filed Aug. 9, 2000, and claims priority thereof.

LASER DRIVEN ION ACCELERATOR

The United States Government has rights in this invention pursuant to Contract No. W-7405-ENG-48 between the United States Department of Energy and the University of California for the operation of Lawrence Livermore National Laboratory.

FIELD OF THE INVENTION

This invention relates to method and apparatus for accelerating particles and, more particularly, to a method and apparatus of accelerating particles to achieve optimal energies.

BACKGROUND OF THE INVENTION

Conventional radiation therapy utilizes electron beams and x-rays as a means of treating and controlling cancer. Due to the inability of current technology to preferentially deposit the radiation at the site of the cancer, healthy tissues between the tissue surface and the cancer also receive high doses or radiation and, therefore, are damaged. Consequently, physicians use a less-than-optimal dose to reduce the undesirable damage to healthy tissues and the subsequent side effects. In many cases, this proves to be an unacceptable alternative.

SUMMARY OF THE INVENTION

Aspects of the present invention include an accelerator system having a light source; and a target having a concave shape.

Aspects of the present invention further include a method including firing a laser pulse having an energy range of approximately 1 to approximately 10 Joules from a light source at a target; guiding radiation elements emitted from said laser pulse striking said target; discriminating ions having a predetermined energy range from said radiation elements; and delivering said ions in an energy range of approximately 10 to approximately 500 Mega-Electron Volt (MeV) to a treatment field.

BRIEF DESCRIPTION OF THE DRAWINGS

The accompanying drawings, which are incorporated into and form a part of the disclosure.

DETAILED DESCRIPTION OF THE INVENTION

Figure 1A:
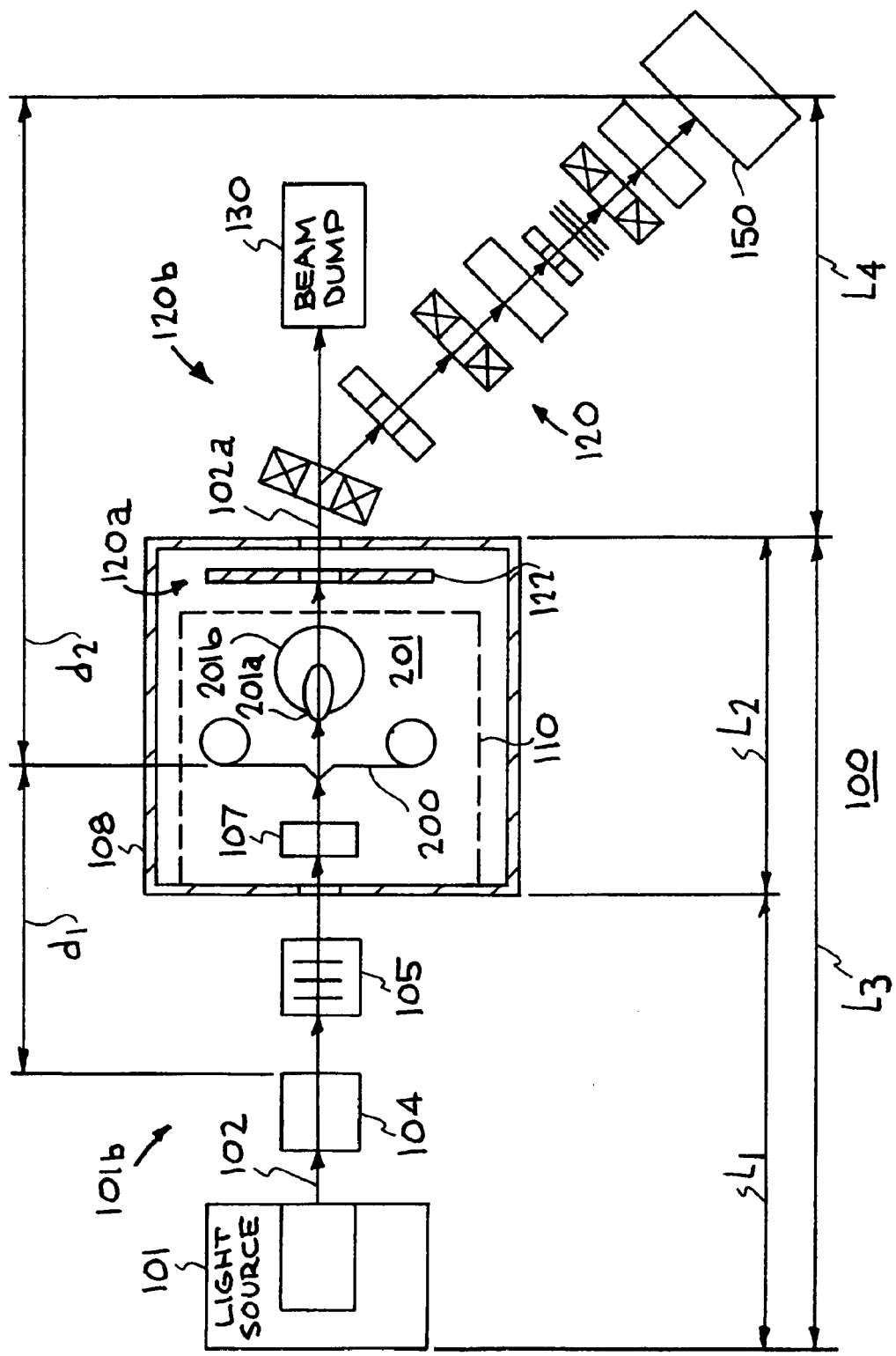
FIGS. 1A–1C illustrate a schematic diagram of a first embodiment of an accelerator system.

Disclosed herein are described accelerator systems and methods which may deliver protons and other ions to higher energies in an efficient manner. The accelerator systems and methods described herein may be in a compact or portable form to increase the flexibility of its use. Exemplary applications of the disclosed accelerator systems and methods may include radiation oncology; ion radiology; ion isotope sources; pion, muon, and neutrino beams sources; and spectroscopic diagnosis (nondestructive or otherwise) of different types of materials. For illustrative purposes, the exemplary embodiments disclosed herein may be used in radiation oncology applications.

FIGS. 1A–1E illustrate a schematic view of an embodiment of an accelerating system 100. The accelerating system includes the following components: a light source system (e.g., laser system) 101 producing an energy pulse 102 which travels through a light source guide system 101b to a target system 110 located in a vacuum chamber 108. The pulse 102 strikes the target 200 in the target system 110 and an ion beam 102a is produced which travels through an ion beam transport system and irradiation system 120 to a treatment field 150. The operation of the accelerating system 100 is controlled by a controller 160 and feedback system 170. These components may combine to form a compact (e.g., portable, tabletop) accelerating system. The length, L1, of the light source system 101 and light source guide system 101b may be in the range of approximately 1 to approximately 2 meters. The length, L2, of the target system 110 and a first section 120a of the ion beam transport and irradiation system 120 may be in the range of approximately 1 to approximately 2 meters. Therefore, the overall length of the light source system 101, light source guide system 101b, the target system 110 and a first section 120a of the ion beam transport and irradiation system 120, L3, may be in the range of approximately 2 to approximately 4 meters. The length, L4, of separation of the vacuum chamber 108 and the treatment field (or object) 150 may vary depending on the specific application. For example, L4 may range from approximately 0.25 to approximately 10 meters. It is to be understood that these exemplary lengths may vary higher or lower, again, depending on the specific application.

The accelerating system 100 is controlled by a controller 160 whose functions will be described in detail below. In order to maximize a flux of ions produced in the accelerator system 100, a chirped-pulse amplification (CPA) based, compact, high-repetition, high fluence laser system (e.g., a Ti: sapphire laser) may be utilized as a light source system 101. The basic configuration of such a light source system 101 is described in U.S. Pat. No. 5,235,606, issued Aug. 10, 1993 to Mourou et al., which is hereby incorporated by reference. The light source system 101 having a pulse shaper 101a emits an energy pulse (or pulses) 102 having a pulse energy of approximately 1 to approximately 10 Joules (J). The pulses 102 may be delivered at a rate of approximately 0.1 to approximately 100 Hertz (Hz). The pulses 102 are transported by a light source guide system 101b which may include a series of mirrors 104 and thin foils 105. Mirrors 104 are configured to guide and focus the pulse 102 with a predetermined intensity using the last mirror in the mirror series 104. Before the pulse 102 enters the target system 110, the light source guide system 101b may include a series of thin foils (e.g., metal) 105 that are capable of controlling or reducing the prepulse of each pulse 102. The prepulse section of each pulse 102 may comprise a field of the pulse 102 prior to the arrival of the main peak of the pulse 102. Because a pulse 102 may be very short and intense, even a fraction of the peak intensity of the pulse 102 (e.g., the prepulse) may be sufficient to ionize and/or ablate the foils 105. The prepulse may be controlled by using multiple foils 105 and a pulse shaper 101a in the light source system 101. The pulse shaper 101a may optionally include a frequency multiplier.

Figure 1B:
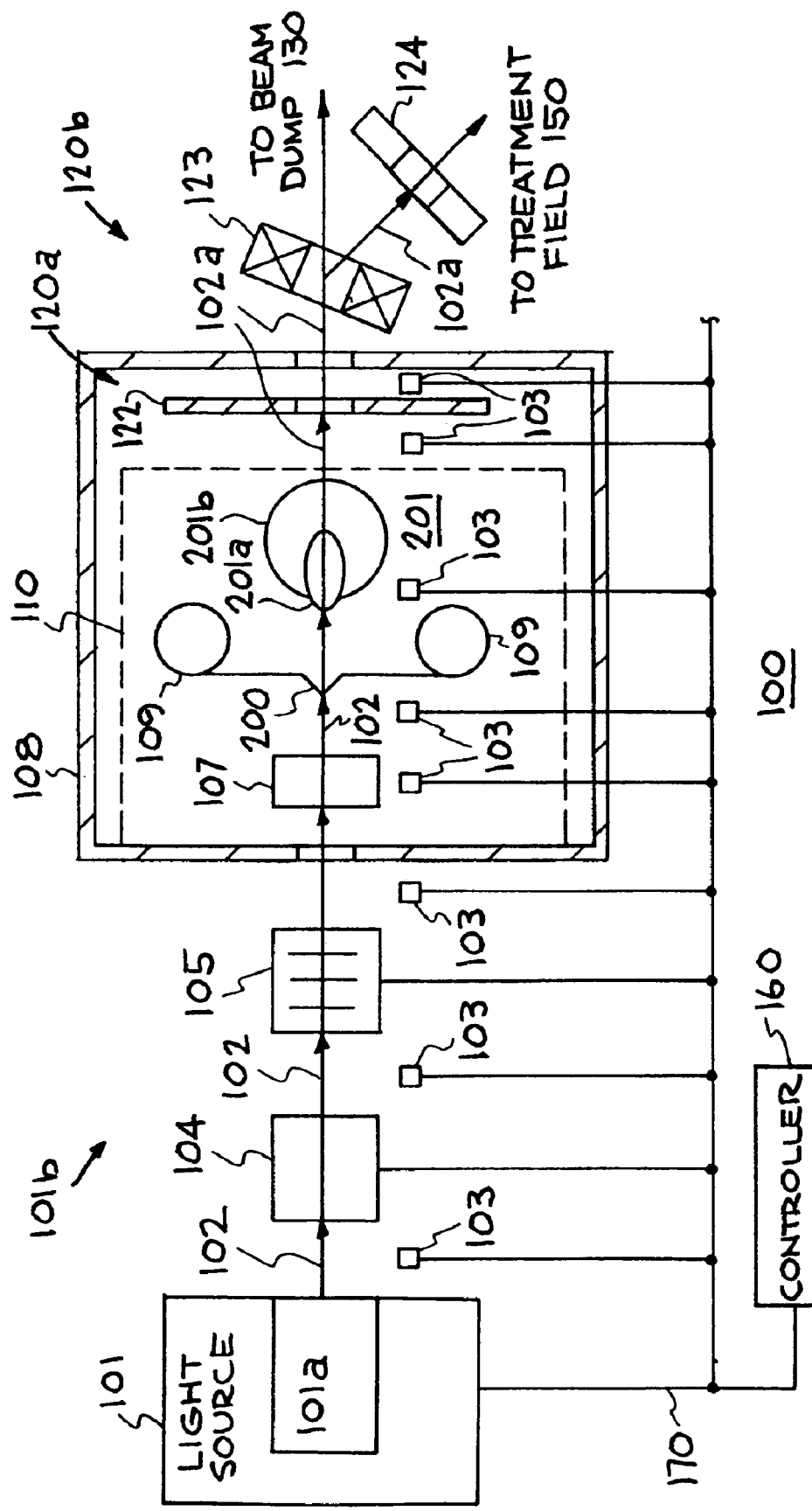
Figure 1C:
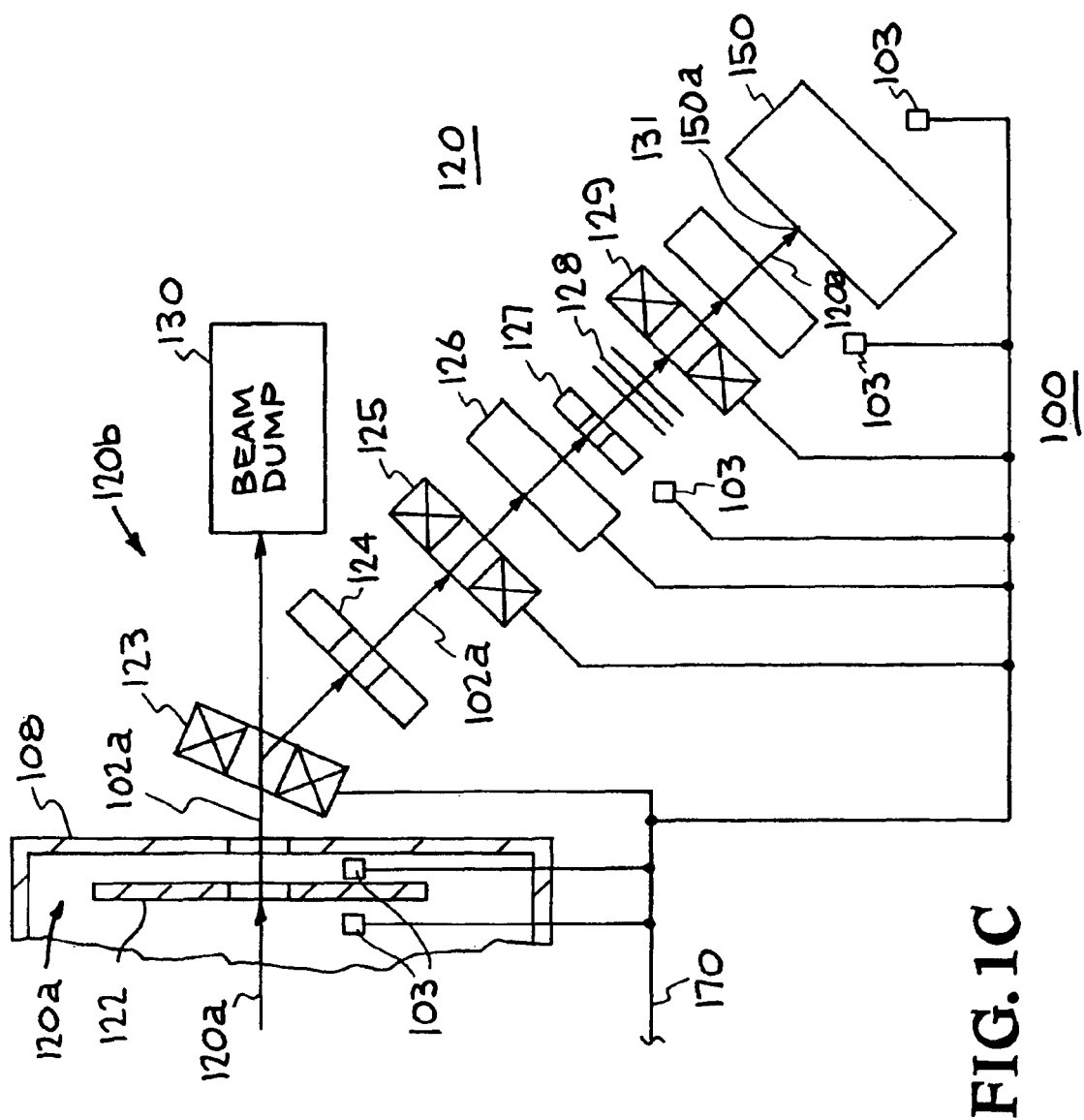

Controller 160 and feedback system 170 are configured to perform monitoring, controlling and feedback functions for the accelerator system 100. Controller 160 may be a microprocessor or other conventional circuitry. A plurality of sensors 103 monitor the intensity of the pulse 102 and ion beam 102a throughout the accelerator system 100. As illustrated by FIGS. 1B and 1C, monitoring points where sensors 103 are positioned may include the light source system 101 output, mirror series 104 output, the target entry point of the pulse 102, after the target 200, before slit 122, before magnets 123, after filters 126, and before and after the treatment field 150. In alternative embodiments, it is to be understood that sensors 103 may not be limited to these numbers or positions. The monitoring information is forwarded through the feedback system 170 to the controller 160. Based on this input, controller 160 is configured to fine-tune the light source system 101 and may provide control signals to light source 101, mirror series 104, foils 105, magnets 123, 125, 129 and filters 126 to adaptively control the quality of pulse 102 and ion beam 102a. Parameters of the pulse 102 and ion beam 102a which may be adaptively controlled by the controller 160 and the feedback system 170 may include repetition rate, laser flux, focus, aperture, angle, intensity, and pulse length.

The pulses 102 may be guided by the a light source guide system 101b into vacuum chamber 108 which encloses target system 110. The target system 110 may be composed of prefoils, target feed, slits and shields represented by reference numeral 107 and a target 200. (Target 200 may also be referred to herein as a foil, a film, a source and accelerator element, or an interaction element). Pulses 102 may be intense, ultrafast (i.e., having a pulse length between approximately 1 to 500 femtoseconds (fs)) and ultra-relativistic. During operation, the pulses 102 immediately (within a few fs of the pulse entry to the target 200) and substantially destroy the target 200 and ionize multiple electrons per each of the atoms contained in the target 200 to form "hot" electrons. Hot electrons may be defined as electrons having energy greater than approximately 1 MeV. Together with conduction band electrons, these hot electrons form a high density electron cloud 201b in region 201 that is driven forward by the acceleration and heating of these electrons to high energies by the light source system 101. An electrostatic field is set up through charge separation by these hot electrons. Therefore, according to a simple one-dimensional model, an accelerating gradient $E_0$ is wavelength, $\lambda$, proportional to the energy (or temperature) of hot electrons divided by the width of the charge separation, which is approximately the Debye length $\lambda_D$ of hot electrons:

$$E_0 = \alpha T_h/\lambda_D,$$

where $\alpha$ is a constant (about 5 to 10) and $T_h$ is the energy of hot electrons. The energy gain of ions may be the following:

$$E_I = ql\, E_0,$$

where q is the ion charge and l is the acceleration distance. Therefore, $$E_I = \alpha q (l/\lambda_D) T_h.$$

When l is approximately $\lambda_D$, which is the case for a simple one-dimensional geometry, an energy gain of ions is obtained as $$E_I \approx ql\, E_0.$$

Based on these equations, the acceleration system 100 is designed to enhance $E_I$ by increasing $\alpha$, $l/\lambda_D$, and $T_h$ (and except for protons, q also).

Figure 2:
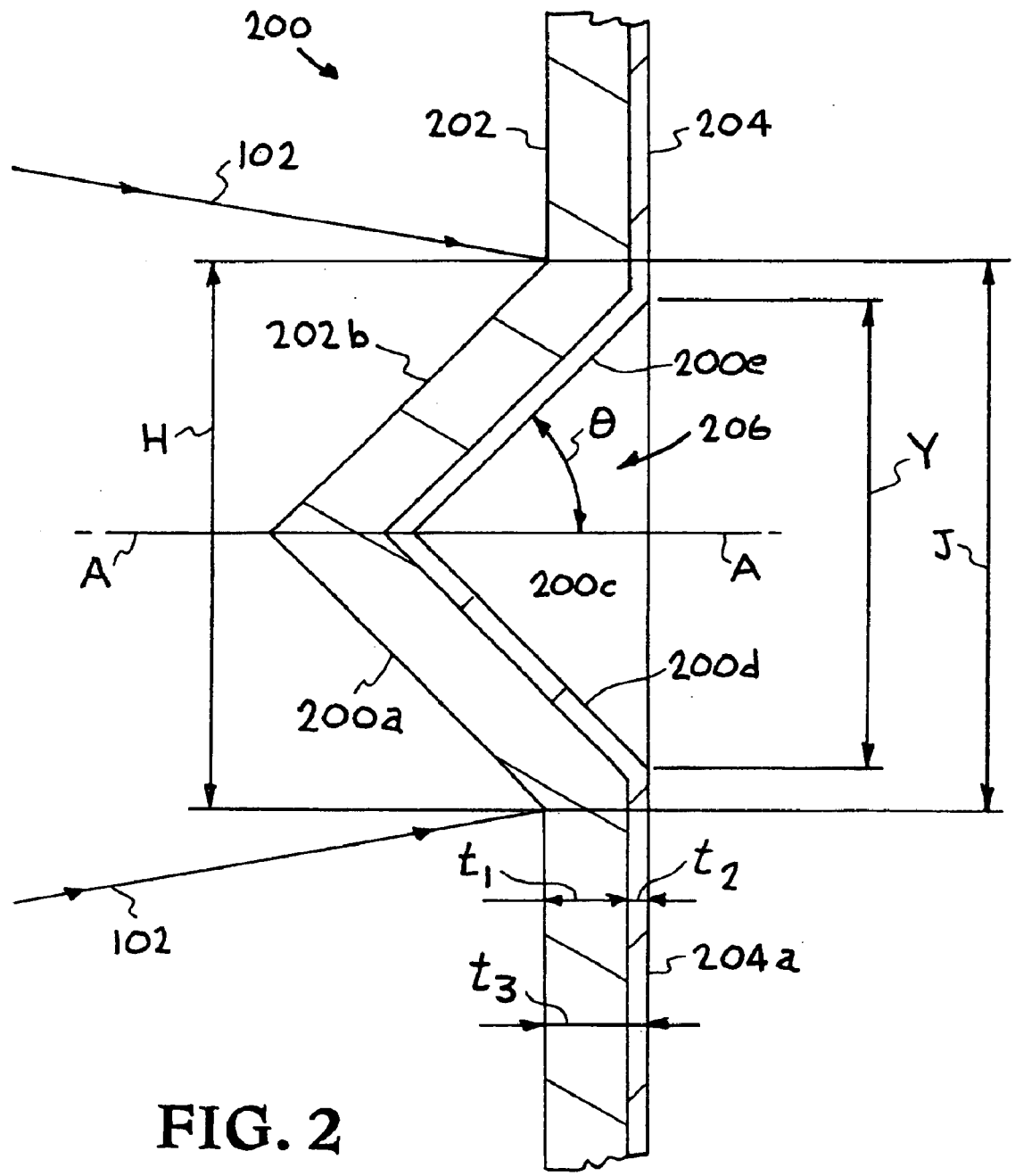
FIG. 2 is a side view of a target used in the accelerator system of FIGS. 1A–1C.

For example, when the geometry of the target 200 has a substantially concave geometry as shown in FIG. 2, both $\alpha$ and l may be increased. If electrons are heated or accelerated to higher energy, $T_h$ (or even $T_h/\lambda_D$) increases. This is because $\lambda_D$ is proportional only $T_h^{1/2}$. The changing target parameters (which are discussed in detail below) may increase $\alpha$, l, or $T_h$, or all of these.

During operation, the energy of the light source system 101 may be compressed into an ultrashort time scale of approximately 10 to 100 fs after a CPA's time stretcher and compressor (not shown), but before the final focal mirror in the mirror series 104. The final focal mirror in the mirror series 104 may focus the pulse 102 which has been time-compressed into a spatially compressed light spot (H in FIG. 2) on the target 200 in the target system 110. The distance, d1 (as shown in FIG. 1A), from the final focal mirror in the mirror series 104 to the target 200 may be substantially less than 1 meter (m). The light source system 101 is capable of delivering to the target 200 a light beam intensity in the range of approximately $10^{18}$ to $10^{23}$ Watts (W)/centimeter $(cm)^2$, with approximately $10^{21}$ W/cm$^2$ being the typical intensity. The target system 110 is designed to allow the optical interaction of the intense short pulse 102 with the target 200 to yield a high flux of energetic ions such as protons 201a (as shown in FIG. 1B). As discussed above, the target 200 may be substantially destroyed when struck by the pulse 102, forming a plasma 201b containing electrons and ions (e.g., protons 201a) in region 201. The plasma electrons may then be driven towards the first section 120a of the ion beam transport and irradiation system 120 and the plasma electrons may pull ions with them towards the first section 120a. The distance from the target 200 to the treatment field 150, d2, may also be less than approximately 1 m. Therefore, the combination of distances d1 and d2 may be less than approximately 1 m. The target 200 may be a film or foil that is rolled into position on rollers 109 under control of controller 160 for each shot of the light source system 101. The target 200 may include a target portion and a prepulse controller portion which controls the prepulse of the pulse 102 or reduces it. Both target portion and prepulse controller portion may be moved synchronously with the pulse shots from light source 101 to expose a fresh film surface. The target 200 will be discussed in further detail below.

The first section 120a of the ion beam transport and irradiation system 120 is located inside vacuum chamber 108. The second section 120b of the ion beam transport and irradiation system 120 is located between the vacuum chamber 108 and the treatment field 150. The first and second sections 120a, 120b of the ion beam transport and irradiation system 120 may include slit 122, magnet or magnets 123, beam dump 130, shields 124, magnet or magnets 125, filter or filters 126, aperture or apertures 127, foil or foils 128, magnet or magnets 129, optional electronic guide 131 and sensors 103. The first and second sections 120a, 120b may include other transportation and control elements not shown in FIGS. 1A–1C. Second section 120b may optionally include a support of the treatment field 150 for irradiation of a patient (support is not shown) in oncological applications.

The ion beam transport and irradiation system 120 is configured to discriminate among various radiation components produced by the pulse 102 striking the target 200. The ion beam transport and irradiation system 120 is designed to achieve this discrimination by isolating predetermined energy ions which are to be used in irradiating the treatment field 150 and separating (i.e., dumping) the radiation components which are not to be used in the irradiation on the treatment field 150. The radiation components which result from the pulse 102 striking the target 200 include different species of ions (e.g., protons), x-rays, electrons, remnants of the pulse 102, and different energy components (e.g., MeV, 10's MeV, and 100's MeV within a certain energy band or window). After ion generation from the target 200, ions such as protons 201a with a predetermined emittance are allowed to pass through the slit 122 in the form of an ion beam 102a. Beyond the slit 122, magnets (or magnet) 123 are designed to discriminate the energy of the predetermined protons (and other types of radiation) by bending the different species and components of radiation and directing the remaining portion of the ion beam 102a into beam dump 130. The magnets 123 may be pulsed as well as electronically modulated for control as well as for scanning. Combined with the magnets 123 are shields 124 and filter or filters 126 which may also be used not only to protect undesired radiation from hitting the treatment field 150 for irradiation, but also to define and discriminate a predetermined portion of the phase space of the given radiation component to be delivered to the treatment field 150. A beam aperture 127 may be used to control the size of the beam 102a to irradiate the treatment field 150. A plurality of high Z metallic foils 128 may be configured inward to stop low energy or low ranged components of radiation and monitor the ion beam 102a. Magnet(s) 129 may control the direction of the ion beam 102a. An optional electronic guide 131 may be placed after the magnet(s) 129 to perform a scanning function of the ion beam 102a on the treatment field 150.

The width, angle and emittance of the ion beam 102a which strikes the treatment field 150 is controlled by a combination of accelerator system 100 design choices. These design choices may include the nature of the target 200 (which will be discussed in detail below), the light source system 101 intensity and focus, the distance of the light source system 101 from the target 200, the choice of transport elements (e.g., magnets, filters, foils, shields, mirrors, and slits), the width of the beam aperture 127, and the use of an optional electronic guide 131. The size of the light source (e.g., laser) spot 150a on the treatment field 150 may vary from about 0.5 to about 20 $cm^2$ in area in accordance with accelerator system 100. For example, a pointed, small emittance beam (i.e., a pencil beam producing a light source spot 150a of approximately 0.5 to approximately 2 $cm^2$) on the order of approximately 1 millimeter milliradians (mm mrad) may be produced by the accelerator system 100. Such a small pencil beam may be configured to scan through the electronic guide 131 and cover a portion of or the whole region of the treatment field 150 by scanning in a predetermined pattern where irradiation is desired. Therefore, in oncological applications, a small tumor (i.e., in the range of approximately 5 to 20 cm) may be more accurately targeted for localized or conformal treatment.

The optical elements (e.g., mirror series 104), target 200, the magnets 123, 125, and 129 and other transport elements may be controlled adaptively through the controller 160 and feedback system 170 during and after each shot from light source system 101. Through the use of the controller 160 and feedback system 170, the control and modulation of the beam energy, energy band, size, and repetition rate may be achieved—shot by shot—of the light source system 101. The ion beam transport and irradiation system 120 may also be configured to discriminate a portion or portions of the ion beam 102a in angle and size to adjust the beam's size, emittance, and flux for predetermined ion beams 102a which allows for a highly flexible system.

At least four parameters of the target 200 may be varied to obtain a change in performance of the ion beam 102a which strikes the treatment field 150. These four parameters may include the width, material, geometry (or shape) and surface of the target 200. The modification of these parameters allows for the maximization of the interaction of the pulse 102 and the target 200 and the maximization of the energy and flux of the ion beam 102a which results from the pulse 102 striking the target 200. A detailed discussion of the four parameters follows.

The pulse 102 which strikes the target 200 has a field (e.g., laser field) with an intensity in the ultra-relativistic region. In the ultra-relativistic region, the electron momentum in the field exceeds mc, where m is the electron rest mass and c the speed of light, so that the electron energy in the field far exceeds that of electron rest mass (e.g., at least approximately $10^{21}$ W/$cm^2$). The pulse 102 may be irradiated over a small spot 200a (as shown in FIG. 2) (e.g., approximately 2 to approximately 10 square microns) on the target 200. The target 200 acts as an ion source as well as an accelerator, emitting energetic ions (e.g., protons 201a as shown in FIGS. 1A–1B) in the plasma region 201 behind the target 200. As discussed above, the plasma region 201 is followed in sequence by the ion beam transport and irradiation system 120 which may extract a predetermined band of protons 201a from the plasma region 201. The beam 102a which emerges from the ion beam transport and irradiation system 120 will be an ion (e.g., proton) beam and is capable of irradiating the treatment field 150 of a patient.

FIG. 2 illustrates an enlarged side view of the target 200. The first parameter of the target 200 that may be varied is the material of the target 200. The target 200 may be a multi-layer material having a first layer 202 and a second layer 204. These layers 202, 204 may be two different materials or bi-material (e.g., bi-metal). The layers 202 and 204 may be adhered together. The first layer 202 of the target 200 is designed to reflect the low-intensity prepulse of the pulse 102 and become transparent at higher intensities of the pulse 102 very quickly after being struck. The first layer 202 may be a metal or semiconducting film material. The first layer 202 may be made of a higher Z material than the second layer 204. For example, first layer 202 may be aluminum, carbon, gold, or lead. A high Z material may contain high atomic number atoms that generate a large number of electrons, but ions in this setting do not gain much energy, while most of the pulse energy is absorbed here. The first layer 202 is capable of converting the photon momentum of the pulse 102 which strikes the target 200 into electron momentum. The first layer 202 may also compress the pulse 102 further by a small factor so that the intensity of the pulse increases at the moment of its impingement on the surface of the target 200 by the electromagnetic (EM) ponderomotive drive of electrons into the interior of the first layer 202. The second layer 204, on the side of the target 200 opposite to the entry of the pulse 102, may be made of proton rich lower Z materials (e.g., hydrogen, hydrogen rich materials, plastics made of carbon, and water) than the first layer 202 material. Low Z materials contain low atomic number atoms that do not generate as many electrons, but generate light ions (e.g., protons, carbon, oxygen ions) and cause a strong electrostatic field. This electrostatic field may convert electron energy into ion energy. The second layer 204 may produce protons through irradiation leading to ionizing the material in the second layer 204 instantaneously (i.e., a range of about 1 to about 5 femtoseconds). Therefore, the first and second layer configuration may enhance electron production in the high Z material of the first layer 202 and stabilize the hot electron production and subsequent ion production. Although a first and second layer are illustrated, it is to be understood that further layers may also be used.

The second parameter of the target 200 that may be varied is the thickness, $t_3$, of the target 200. The thickness $t_1$ of the first layer 202 is designed to be large enough to stop substantially all of the pulse 102. However, it may not be designed to be so large as to capture hot electrons generated by the first layer 202. The typical thickness $t_1$ of the first layer 202 is also dependent and inversely proportional to the Z value of the material and, therefore, the stopping power. The range of the thickness $t_1$ may be approximately 50 to approximately 2000 nanometers (nm). If the prepulse of the pulse 102 from the particular light source system 101 varies longer and larger so as to ablate the first layer 202, the thickness $t_1$ may be increased accordingly. The thickness $t_2$ of the second layer 204 may be smaller than the first layer 202 and in the range of approximately 10 to approximately 2000 nm, and, typically in the range of approximately 10 to approximately 100 nm. Therefore, the combined thickness of the first and second layers to form the thickness of the target, $t_3$, may be in the range of approximately 60 to approximately 2500 nm.

The third parameter of the target 200 that may be controlled is the shape of the target 200. The geometry (or geometries) of the target 200 may enhance the electron density and the ability to trap ions behind these electrons, thereby increasing both $\alpha$ and l. In order to enhance the accelerating electrostatic field that results from the pulse 102 striking the target 200 and the capacity to capture protons, the geometry of the target 200 may be substantially concave toward the acceleration direction as shown by reference numeral 206 in FIG. 2. In addition, this concave configuration allows direct drive of electrons out of the target 200 into the hollow 200c of the concavity 206 of the target 200 by an electric field caused by the light source (e.g., a laser field) as the angle θ between the target surface and the pulse incident direction allows greater energy and population of electrons driven out of the target 200. Furthermore, the concave geometry introduces the ability to control the ion beam optics, such as the focusability, emittance and enhanced density of the ion beam 102a. In alternative embodiments, a plurality of concavities may be used instead of a single concavity.

As discussed above, reference numeral H indicates the spot size of the pulse 102 as it reaches the target 200. The first or light source side diameter J of the concavity facing the pulse 102 may be made substantially equal to the spot size H and the second or non-light source side diameter Y of the concavity 206 may be less than the spot size H. H, J and Y may each have a radius in the range of approximately 1 to approximately 10 microns. In alternative embodiments, H, J and Y may be designed to be substantially different in dimensions. For example, J may be substantially less than H or H may be substantially less than J. The concave shape of the target 200 may determine the focusability of ions (e.g., protons) depending on the curvature of the concavity 206. Varying the aspect ratio of the concavity 206, or the ratio of the diameter Y to the concavity measurement of concavity 206 (i.e., the slant of walls 200d and 200e off axis A—A), may change the focal length of the target 200. The smaller the aspect ratio, the shorter the ion focal length. The ion beam 102a emittance may be determined by the spot size H on the target 200 times the angular divergence of the ion (e.g., proton). The angle, θ, of the concavity measurement of concavity 206 (i.e., the slant of walls 200d and 200e off axis A—A), may be in the range of approximately 10 to approximately 90 degrees and, typically, may be approximately 40 to approximately 50 degrees. The angle, θ, of the concavity measurement of concavity 206 with respect to the first and second layers 202, 204 (and the plane parallel to the phase front of the incident pulse 102) may cause the transverse electric field of the pulse 102 to directly drive electrons into the first layer 202 and thereby enhance the energy of electrons coming off this first layer 202 to be higher. The nature of the concavity 206 may hold these electrons from dispersing to sustain a high density that sets up a high accelerating electrostatic field in the region 201. The concave geometry of target 200 allows the charge of the electron cloud accelerated off the first layer 202 to see image charge not only behind the charge, but also beside it.

Figure 3A:
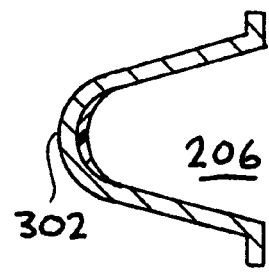
FIGS. 3A–3E are alternative target configurations that may be used in the accelerator of FIGS. 1A–1C.
Figure 3B:
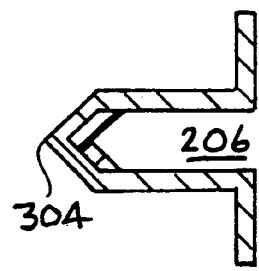
Figure 3C:
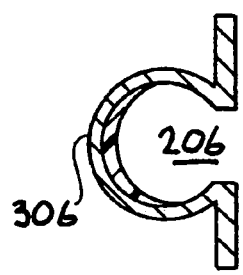
Figure 3D:
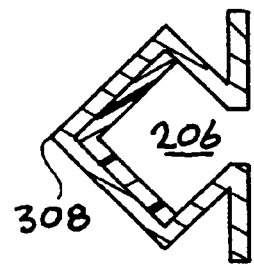
Figure 3E:
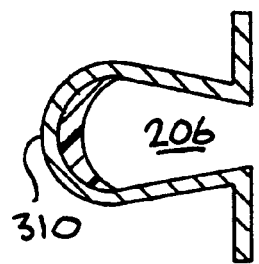

FIGS. 3A–3E illustrate a series of alternative designs for the concavity 206 of target 200. FIG. 3A illustrates a concavity 206 with a dome shape having a base wider than a narrower curved shape at the distal end 302. FIG. 3B illustrates a concavity 206 with a substantially pointed distal end 304. FIG. 3C illustrates a concavity 206 having an enhancement of the concave feature by increasing the angle of the concavity wall and, therefore, having a substantially circular shape 306. FIG. 3D illustrates a concavity 206 with a polygonal shape 308 with walls being extremely angled. FIG. 3E illustrates a concavity 206 with a base being narrower than a substantially curved shape at the distal end 310. These different concavity configurations allow electrons to propagate forward less impeded by the electrostatic force set up between the electrons and ions (which, otherwise, might turn the electrons back before the ions get accelerated), while ions are allowed to gain momentum to reduce the impedance mismatching between electrons and ions. The concave nature of the target 200 also allows the electrostatic fields and magnetic fields which are formed to pinch the electrons toward the axis (A—A in FIG. 2) of the concavity 206, thereby increasing their density, which can induce axial electric current and the induced azimuthal magnetic fields further. These magnetic fields may further pinch the electron stream and increase the electron density and accelerating fields.

Figure 4A:
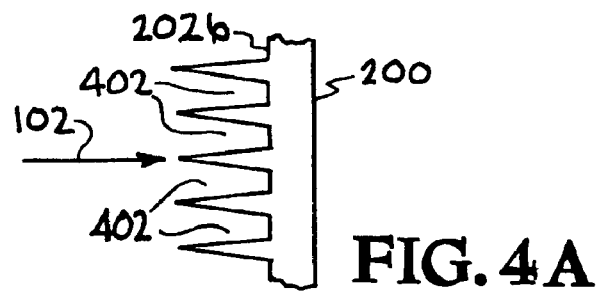
FIGS. 4A–4E are alternative target surfaces that may be used in the accelerator system of FIGS. 1A–1C.
Figure 4B:
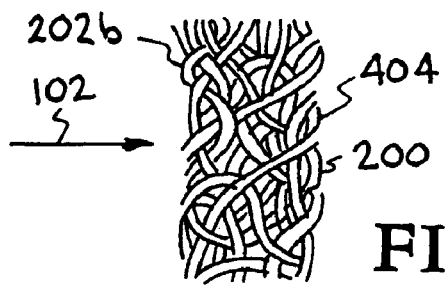
Figure 4C:
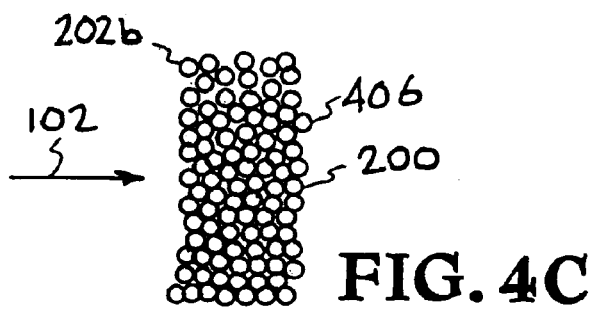
Figure 4D:
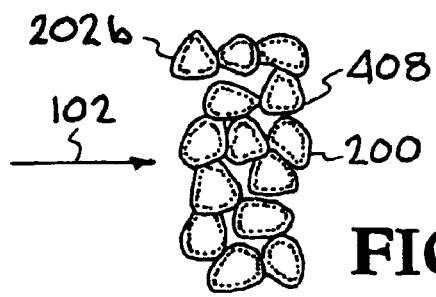
Figure 4E:
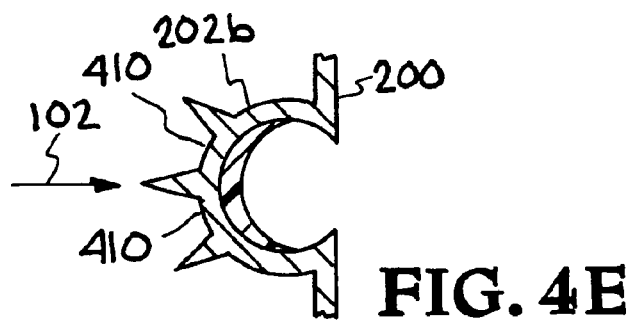

The fourth parameter that may be controlled of the target 200 is the design of the surface 202b (as shown in FIG. 2). The target material surface preparation may be designed so that pulse absorption is more efficient and resultant electron energy is greater. In order to enhance the absorption of the pulse 102 and the production of energetic electrons that drive the accelerating field of protons, the surface 202b of the first layer 202 may be roughened. In another embodiment the surface 202b of the first layer 202 may have at least one groove which has a depth and width of less than approximately 1 micrometer, and, typically in the range of approximately 10 to approximately 100 nm. FIG. 4A illustrates a surface 202b of the target 200 having a plurality of grooves 402. FIG. 4B illustrates a surface 202b having fibers (e.g., thin fibers) 404. FIG. 4C illustrates a surface 202b having clusters 406 of approximately 10 to approximately 100 nm in diameter. Clusters from originally gaseous material may be made by spraying a gas jet into a vacuum. Another method of creating clusters may be found in U.S. Pat. No. 5,585,020, issued Dec. 17, 1996 to Becker et al. and hereby incorporated by reference. The packing ratio of the clusters may be defined as the ratio of the space occupied by clusters and that unoccupied by clusters. The packing ratio of the clusters may be high, specifically, up to about 1:1. A method of forming these clusters may include spraying or adsorbing them onto the second layer 204 of target 200 on the side facing the pulse 102. FIG. 4D illustrates a surface 202b composed of foams 408 of approximately 10 to approximately 100 nm in diameter. FIG. 4E illustrates a combination rounded concavity with grooves 410. The surface preparations illustrated in FIGS. 4A–4E are conducive of enhanced absorption of pulse 102 over a short distance which may be approximately less than 1 micron. For example, clusters 406 may be capable of absorbing nearly all (i.e., greater than approximately 70%) of the pulse energy when the pulse 102 has enough intensity. The size of grooves 402, fibers 404, clusters 406 or foams 408 may be designed to be shorter than the size of electron excursion in the pulse field (less than approximately 1 micron). For example, in the case of carbon such material may be soot. In alternative embodiments, hydrogen atoms may be adsorbed onto the back surface 204a (the surface opposite to the direction of the laser pulse 102 as shown in FIG. 2) of the target 200. In order to further control the prepulse of pulse 102, several methods may be used. As discussed above, in front of the target, in reference numeral 107 (as illustrated by FIG. 1B) there may be placed an additional thin foil that is thick enough to absorb most of the prepulse energy of the pulse 102 but thin enough to be burned by the time the main peak of the pulse 102 arrives.

Figure 5:
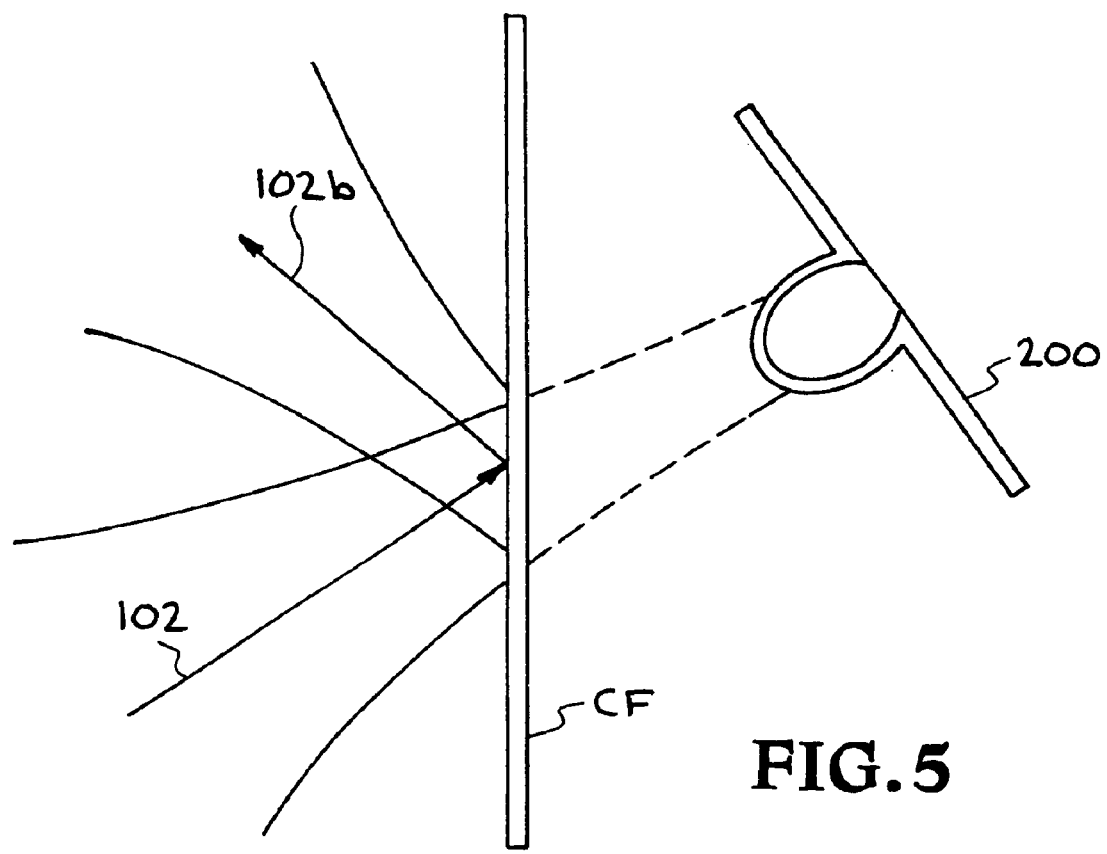
FIG. 5 is a schematic view of a prepulse control structure that may be used in the accelerator of FIGS. 1A–1C.

The material, thickness, geometry and surface design of the target 200 may be predetermined depending on the specific light source system 101 (e.g., laser system) used as well as the feedback system 170 in a shot-by-shot basis. In an alternative embodiment as illustrated by FIG. 5, a prepulse control foil CF may be placed at an angle with respect to the target 200 surface so as to cut off the prepulse of pulse 102 but to transmit the peak main pulse. Most of the prepulse will be reflected as shown by reflected pulse 102b. In another embodiment, a plasma mirror (a mirror made up of a plasma that may be ionized by the light source itself or prefabricated) may be employed before the target 200 that transmits (or reflects) laser light according to its optical property as a function of intensity. In another embodiment, a frequency multiplier (i.e., double or triple) may be placed before the target 200 using a nonlinear crystal so that weaker prepulse components may be cut off (i.e., chopped). In another alternative embodiment, a genetic algorithm (or similar computer software) located in light source system 101 or controller 160 may be used to rearrange the spectrum of the broad band light source system 101 to sharpen the front side of the pulse 102.

When a laser system is used for the light source 101, the laser energy per laser shot from the laser system 101 is typically approximately 1 to approximately 10 J at the target 200, while the obtainable ion energy from the accelerator system 100 may be approximately 10 to approximately 100 mJ at a predetermined energy of approximately 10 to approximately 500 MeV and typically a predetermined energy in the range of approximately 100 to approximately 200 MeV. For a radiation oncology application, a radiation dose of ions (e.g., protons) of approximately 1 to approximately 10 Gray (Gy) on a 1 centimeter (cm)$^2$ area over the 10 cm range of 100 MeV portons, may yield 10 cm$^3$ volume of irradiated tissue. (The range may also depend on factors such as the ion focus size). Therefore, the accelerator system 100 may be capable of producing an ion beam 102a which may penetrate approximately 10 to approximately 20 cm beneath the surface of skin tissue in the treatment field 150 of a patient to reach a tumor sight; produce a dose per shot at the treatment field 150 in the range of approximately 0.1 to approximately 10 Gy; and produce a dose per second at the treatment field of approximately 0.1 to approximately 100 Gy/second. If the light source system 101 repetition rate is approximately 10 Hz, a dose delivered to the treatment field 150 by the accelerator system 100 in less than approximately 1 second may be capable of treating a small tumor target on the order of approximately 1 square cm or less. If the tumor target is larger than approximately 1 square cm, a dose delivered by the accelerator system 100 may be capable of treating the tumor target in less than approximately 1 minute.

Figure 6:
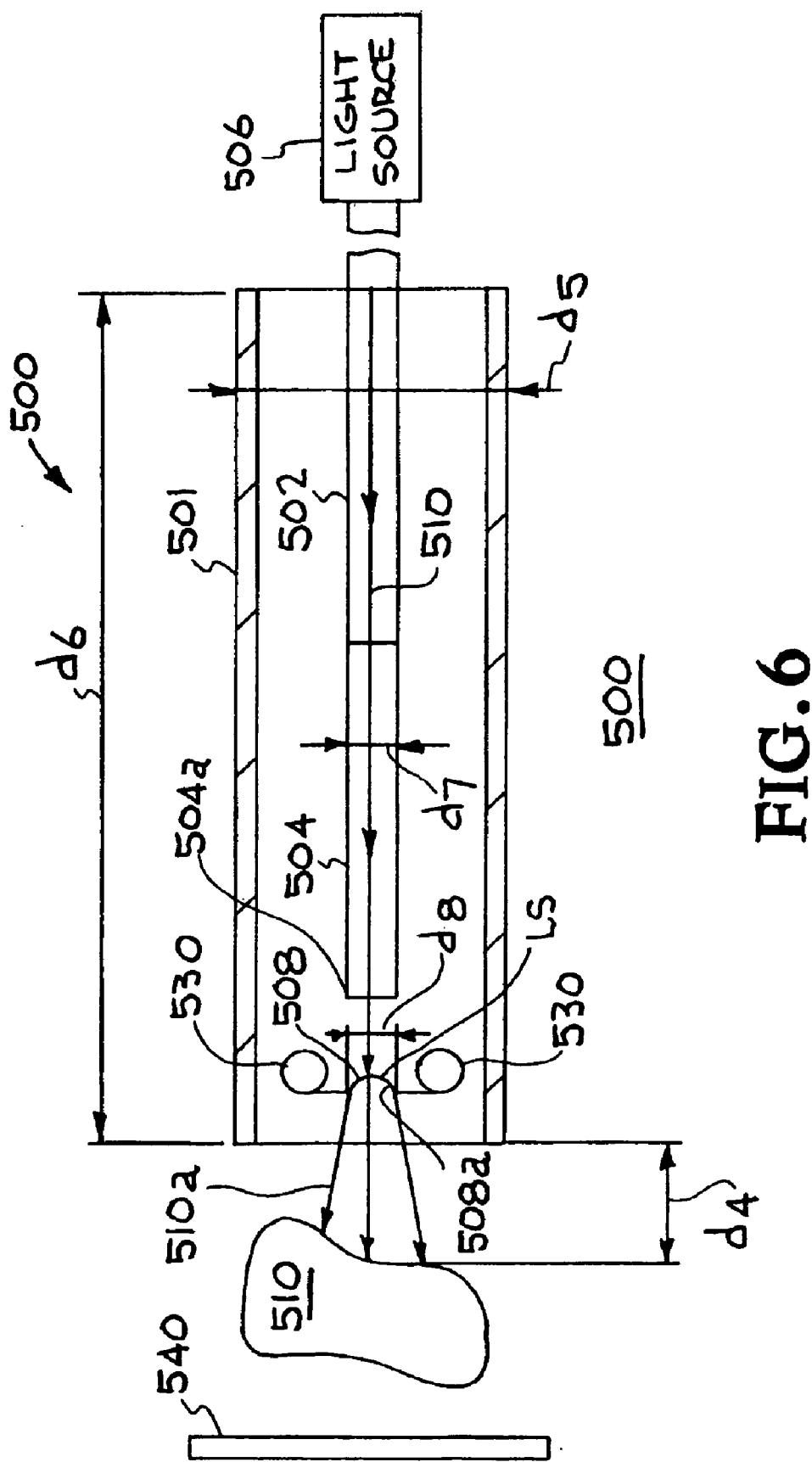
FIG. 6 is a schematic diagram of a second embodiment of the accelerator system.

FIG. 6 discloses an alternative accelerating system and method 500. Housing 501 may be a needle or a syringe. Housing 501 may have a length, d6, of approximately 10 to approximately 40 cm and width, d5, of approximately 50 to approximately 300 microns. Contained within the housing 501 are a first section 502 connected to a second section 504. The first section 502 may be a fiberglass or fiberoptic material and is connected to a light source system (e.g., a laser system) 506 which is capable of producing an energy pulse 510 (e.g., laser pulse). The first section 502 may vary in length depending on the application. Typically, the first section 502 may vary from about 0.1 to 10 meters. A protective surrounding such as housing 501 may be used so that any stray light may be reflected and/or absorbed in case the application of the light source system 506 is to human tissue. The first section 502 and second section 504 are used as a light source guide to a target 508. Target 508 may be rolled into laser shot position (as shown in FIG. 6) through a delivery system such as rollers 530. Typically, the target 508 may be placed in a predetermined position before each shot of the light source system 506. The second section 504 may also be a hollow fiberglass (or fiberoptic) material. The second section 504 may be capable of conducting pulses 510 (e.g., short pulses) with intensity exceeding approximately 10$^{16}$ W/cm$^2$ over a distance of approximately 10 cm. The pulse 510 is propagated through the first section 502 and second section 504 to a spot in proximity to the target 508. The length of the first section 502 is may vary depending on the specific application. Light source system 506 may be a chirped-pulse amplification (CPA) based compact high-repetition, high fluence laser system (e.g., a Ti: sapphire laser). The light source system 506 may be inversely chirped so that as the pulse 510 propagates through the first section 502 and the second section 504 the pulse 510 may contact itself in time domain to yield maximally allowed intensity (e.g., approximately 10$^{17}$ W/cm$^2$). Specifically, the pulse 510 (which was originally time stretched) may, in the first half of the CPA technique, be compressed by a compressor (not shown) only to the extent that the pulse 510 does not exceed a threshold intensity (approximately 10$^{16}$ W/cm$^2$ or less), which may be further compressed through the second section 504. The second section 504 may be constructed such that its fiber radius, length, and index of refraction may be designed so that after the pulse 510 exits the second section 504, the maximum time compression of the pulse 510 may be achieved. The mode of the pulse electromagnetic wave should be that of J$_0$ (i.e., the zeroth order Bessel mode [F.Dorchies et al., Phys.Rev. Lett. vol. 82, p.4655 (1999)]) to avoid surface damage on the fiber of second section 504. The pulse length at the target 508 irradiation is designed to maximally excite the shock wave resulting from the pulse striking the target 508. The tip 504a of the second section 504 may be replaceable if necessary after the material damage caused by the pulse 510 and/or radiation.

The diameter d7 of the second section 504 may be approximately 30 to approximately 500 microns, and typically, approximately 75 to approximately 125 microns. The resulting laser spot LS on the target 508 also has a size d8 of approximately 100 microns. The accelerated number of protons is approximately $10^{11}$ per laser shot with typical proton energies of approximately 1 MeV. The resulting ion (e.g., proton) beam 510a is directly irradiated on the treatment field 510 (e.g., biological issues) from a distance d4 which may in the range of approximately 0.1 to approximately 10 millimeters. After the treatment field 510, a backscatter film (e.g., higher Z metal such as aluminum (Al)) 540 may be positioned with a thickness of approximately 10 to approximately 50 microns to absorb radiation. Backscatter film 540 serves to backscatter x-rays toward the treatment field 510. Therefore, the geometry of the backscatter film 540 may be straight as shown in FIG. 6 or concave or another shape that surrounds the treatment field 510.

Target 508 may be constructed in several ways. The target 508 may be constructed by varying at least four design parameters (thickness, material geometry, and surface) similarly to the target 200 as discussed above with respect to FIGS. 1–4E. In another embodiment, target 508 may be a thick, dense film such as plastic or a metal coated plastic. In another embodiment, target 508 may have a coating of metallic vapor surface designed to face the direction of the pulse 510. In another embodiment, target 508 may be a metallic foil coated with hydrogen gas/liquid (e.g., water) spray 602 on the side facing away from the laser pulse 510. In another embodiment, target 508 may be a spongy material with a porous structure (e.g., hydrocarbon, ceramic, or metals capable of absorbing a large amount of hydrogen or hydrogen rich substance) immersed in hydrogen. In another embodiment, shown in FIG. 7, a foil 704 made of a metallic material (e.g., Al) having a thickness in the range of approximately 10 to approximately 30 microns may be placed spaced apart from target 508 to screen the treatment field 510 from radiations of different characters and energies.

The accelerator system 500 may be used in the case of a medical application such as radiation oncology which allows for the irradiation of a treatment field such as tumorous tissue in situ (or under the skin surface) rather than from the exterior of the patient's body. In accelerating system 500, ions (e.g., protons) are delivered to the spot of the tumor, for example, through a bodily opening or incision. Therefore, the typical energy of 100 to 200 MeV for a 10 to 20 cm range is not required. This type of irradiation is therefore nearly direct without significantly affecting healthy tissues.

The embodiments disclosed in FIGS. 1–5 illustrate a system and method that may enable the delivery of ions (e.g., protons) energetic enough to make sufficiently high radiation dose for oncology and other applications. The disclosed embodiments may operate compactly, flexibly and inexpensively. The disclosed embodiments may be based on a high power compact light source irradiating a target(s) and associated devices described above. Many radiation oncology applications require irradiation of protons from outside of a body. Therefore, these applications may require energies beyond 100 MeV with a dose of approximately 1 Gy. The disclosed embodiments feature a method that may go beyond approximately 100 MeV with sufficient dose and irradiation properties needed for radiation oncology applications. Elements of the disclosed embodiments (which are described above) may include: deployment of intense compact high repetition laser and its conditions (particular laser technology to be deployed, intensity, pulse duration, aperture, and pulse shaping), irradiation of a target whose thickness, material (bimetal or bi-metal), geometry (concave and other variations) and surface (clusters or frustrated surface or other variations) are specified, the focusability and transport of the ion beams by the target geometry and additional magnetic and other transport devices, the prepulse control measures, the flexible adjustment, monitor, and feedback of various parameters of laser, target, optics, transport system, and treatment field, the overall systems concept, which among other things, allow flexible, compact, and inexpensive deployment of this device that includes intra-operative and portable usage as well as potential compatibility with existing treatment facilities. Unlike X-rays and electron beams, ion (e.g., proton) beams have a sharp Bragg peak, enabling the deposition of the precise dose at a predetermined location. With these flexible capabilities enabled in the disclosed embodiments a precise and flexible deposition of radiation dose may be possible. The disclosed embodiments may give rise to energies of beam protons (and other ions) in excess of approximately 100 MeV and doses in the range of approximately 0.01 to approximately 100 Gy, (and typically approximately 1 Gy), over an approximately 0.1 to approximately 100 second period (and typically approximately one second), which are in the range of oncological needs.

Figure 7:
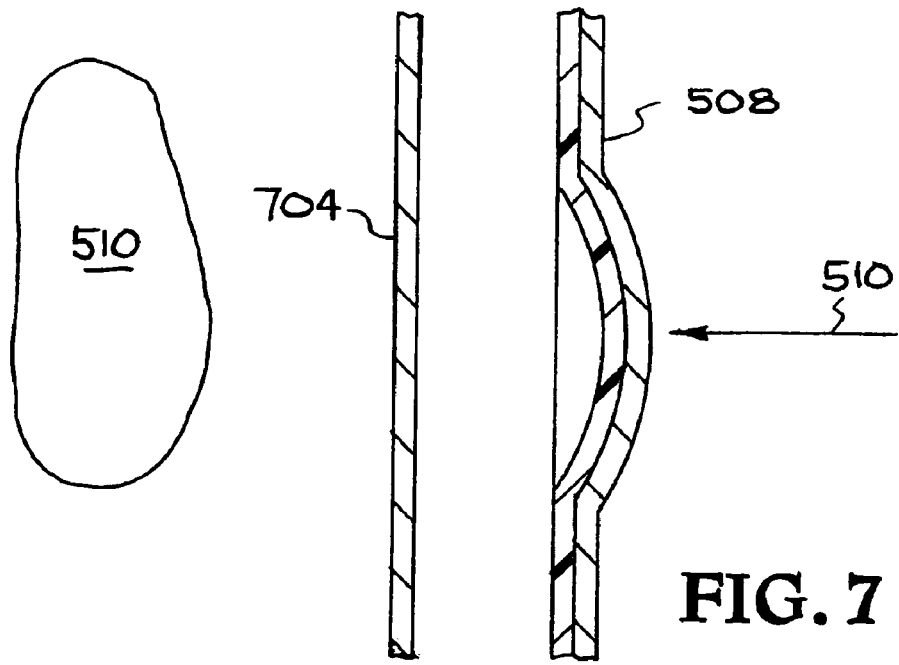
FIG. 7 is a side view of an alternative configuration of a film used in the accelerator system of FIG. 6.

The embodiments disclosed in FIGS. 6–7 allow for a compact delivery of protons, whose energy may be in the range of sub-MeV to several MeV with a similar (or less) dose. Since these embodiments may be inserted substantially adjacent to the location of the treatment field, this energy is sufficient to treat oncological targets.

The foregoing is for illustrative purposes and is not to be construed as limiting thereof. The invention is defined by the following claims, with equivalents of the claims to be included therein.

The invention claimed is:

1. An accelerator for delivering protons or other ions comprising:
   a laser system that produces a laser pulse;
   a target having a first layer and a second layer arranged to receive said laser pulse from said laser system and to produce a beam of protons or other ions;
   a laser pulse transport system operatively coupled to said laser system and said target and having an electronic guide,
   a treatment field, and
   a beam transport system operatively coupled to said target and said treatment field for transporting said beam of protons or other ions from said target to said treatment field.

2. The accelerator system of claim 1, wherein said laser pulse transport system is comprised of elements selected from the group consisting of slits, filters, magnets, foils and shields.

3. The accelerator system of claim 1, wherein the target is operatively connected to at least one roller.

4. An accelerator system for delivering protons or other ions comprising:
   a light source capable of producing an energy per laser shot of between approximately 1 and 10 approximately Joules;
   a target positioned to receive a laser shot from said light source and to produce a beam of protons or other ions;
   a transport system operatively connected to said light source and to said target capable of delivering energy in the range of approximately 10 to approximately 500 MeV to said target, a treatment field, and a beam transport system operatively coupled to said target and to said treatment field for transporting said beam of protons or other ions from said target to said treatment field.

5. The accelerator system of claim 4, wherein said target has a first layer and a second layer; and said first and second layers having a combined thickness in the range of approximately 60 to approximately 2500 nm.

6. The accelerator system of claim 4, wherein said target has a substantially concave shape.

7. A system for delivering protons or other ions comprising:

a light source capable of producing an energy per laser shot of between approximately 1 and approximately 10 Joules;

a target capable of producing radiation elements that produces the protons or other ions;

a transport system operatively connected to said light source and to said target capable of delivering energy per laser shot of between approximately 1 and approximately 10 Joules to said target, a treatment field, and a transport system capable of delivering the protons or other ions which may penetrate about 10 to about 20 cm beneath the surface of skin tissue in said treatment field.

8. A system for delivering protons or other ions comprising:

a light source capable of producing an energy per shot of the light source of between approximately 1 and approximately 10 Joules;

a target capable of producing radiation elements that produces the protons or other ions;

a first transport system operatively coupled to said light source and said target, a treatment field, and a transport system capable of delivering the protons or other ions having energy to produce a dose per shot at said treatment field in the range of about 0.1 to about 10 Gy.

9. A method for delivering protons or other ions to a treatment field comprising the step of:

firing a pulse from a light source;

guiding said pulse through a fiber optic section to a target thereby causing said target to emit the protons or other ions; and delivering the protons or other ions emitted from said target to the treatment field.

10. A method of delivering a radiation dose of protons or other ions to treat an oncological treatment field in a patient comprising the steps of:

firing a pulse from a laser;

guiding said pulse through a fiber optic section to a target thereby causing said target to emit the protons or other ions; and delivering the protons or other ions emitted from said target to the oncological treatment field in the patient.

11. The method of claim 10, further comprising:

positioning said fiber optic section beneath the skin surface of the patient.

* * * * *